United States Patent [19]

Müller et al.

[11] Patent Number: 4,952,233
[45] Date of Patent: * Aug. 28, 1990

[54] HERBICIDAL SULPHONYLAMINOGUANIDINOAZINES

[75] Inventors: Klaus-Helmut Müller, Duesseldorf; Christa Fest, Wuppertal; Rolf Kirsten; Theodor Pfister, both of Monheim; Hans-Jochem Riebel, Wuppertal; Hans-Joachim Santel, Leverkusen; Robert R. Schmidt, Bergisch Gladbach; Harry Strang, Duesseldorf, all of Fed. Rep. of Germany

[73] Assignee: Bayer Aktiengesellschaft, Leverkusen, Fed. Rep. of Germany

[*] Notice: The portion of the term of this patent subsequent to Feb. 16, 2005 has been disclaimed.

[21] Appl. No.: 227,587

[22] Filed: Aug. 2, 1988
(Under 37 CFR 1.47)

[30] Foreign Application Priority Data

Aug. 7, 1987 [DE] Fed. Rep. of Germany ....... 3726269

[51] Int. Cl.$^5$ .................. A01N 43/54; C07D 239/42; C07D 239/48; C07D 239/50
[52] U.S. Cl. .......................... 71/92; 544/321; 544/323; 544/332; 544/324; 544/331; 544/320
[58] Field of Search ................... 71/92; 544/321, 323, 544/332, 324, 331, 320

[56] References Cited

U.S. PATENT DOCUMENTS

| | | | |
|---|---|---|---|
| 4,602,938 | 7/1986 | Moriya et al. | 71/92 |
| 4,725,303 | 2/1988 | Moriya et al. | 71/92 |
| 4,743,294 | 5/1988 | Diehr et al. | 71/93 |

FOREIGN PATENT DOCUMENTS 0121082 10/1984 European Pat. Off.

OTHER PUBLICATIONS

Sevastlyanov et al., Chemical Abstracts, vol. 95, (1981), p. 642.

Primary Examiner—John M. Ford
Attorney, Agent, or Firm—Sprung, Horn, Kramer & Woods

[57] ABSTRACT

Herbicidally active sulphonylamino guanidinoazines of the formula

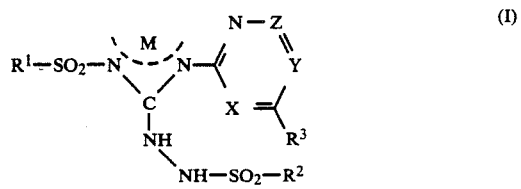

in which
R$^1$ stands for a optionally substituted radical from the series comprising alkyl, aralkyl, aryl and hetaryl, R$^2$ stands for an optionally substituted radical from the series comprising alkyl, aralkyl, aryl, hetaryl and dialkylamino, R$^3$ stands for hydrogen, halogen, hydroxyl, alkyl, halogenoalkyl, alkoxyalkyl, alkoxy, halogenoalkoxy, alkylthio, halogenoalkylthio, amino, alkylamino or dialkylamino,
X stands for nitrogen or a —CH— grouping,
Y stands for nitrogen or a —CR$^4$— grouping,
wherein
R$^4$ stands for hydrogen, halogen, cyano, alkyl, formyl, alkyl-carbonyl or alkoxy-carbonyl,
Z stands for nitrogen or a —CR$^5$— grouping,
wherein
R$^5$ stands for hydrogen, halogen, hydroxyl, alkyl, alkoxy, halogenoalkoxy, alkylthio, alkylamino or dialkylamino, and
M stands for hydrogen, a metal equivalent, an ammonium equivalent, an alkylammonium equivalent, a dealkylammonium equivalent, or a trialkylammonium equivalent, excluding N'-(4,6-dimethyl-pyrimidin-2-yl)-N''-(4-methyl-phenyl-sulphonylamino)-N'''-(2-chloro-phenyl-sulphonyl)guanidine.

10 Claims, No Drawings

HERBICIDAL SULPHONYLAMINOGUANIDINOAZINES

The invention relates to new sulphonylaminoguanidinoazines, a process for their preparation and their use as herbicides.

It has already been disclosed that certain aminoguanidinoazines, such as, for example, N'-(4,6-dimethylpyrimidin-2-yl)-N"-acetamido-N'"-(2-chlorophenylsulphonyl)guanidine exhibit herbicidal properties (compare EP-A No. 121,082).* The herbicidal action of the hitherto known aminoguanidinoazines is not always very satisfactory, however.
(*corresponding to U.S. Pat. No. 4,602,938)

New sulphonylaminoguanidinoazines of the general formula (I)

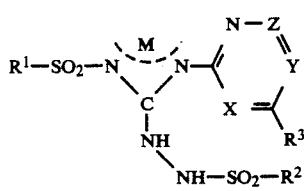  (I)

in which
$R^1$ stands for an optionally substituted radical from the series comprising alkyl, aralkyl, aryl and hetaryl, $R^2$ stands for an optionally substituted radical from the series comprising alkyl, aralkyl, aryl, hetaryl and dialkylamino, $R^3$ stands for hydrogen, halogen, hydroxyl, alkyl, halogenoalkyl, alkoxyalkyl, alkoxy, halogenoalkoxy, alkylthio, halogenoalkylthio, amino, alkylamino or dialkylamino,
X stands for nitrogen or a —CH— grouping,
Y stands for nitrogen or a —$CR^4$— grouping,
wherein
$R^4$ stands for hydrogen, halogen, cyano, alkyl, formyl, alkyl-carbonyl or alkoxy-carbonyl,
Z stands for nitrogen or a —$CR^5$— grouping,
wherein
$R^5$ stands for hydrogen, halogen, hydroxyl, alkyl, alkoxy, halogenoalkoxy, alkylthio, alkylamino or dialkylamino, and
M stands for hydrogen, a metal equivalent, an ammonium equivalent, an alkylammonium equivalent, a dialkylammonium equivalent, or a trialkylammonium equivalent,
have now been found, where N,-(4,6-dimethyl-pyrimidin-2-yl)N"-(4-methyl-phenylsulphonylamino)-N'"-(2-chloro-phenylsulphonyl)-guanidine—known from EP-A No. 121,082 —is excluded.

The general formula (I) stands—when M stands for hydrogen—for the individual possible tautomers of the formulae (IA), (IB) and (IC)

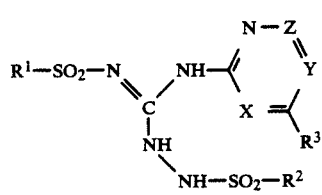  (IA)

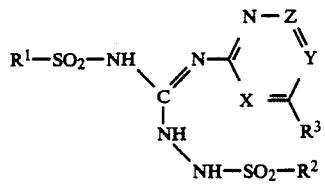  (IB)

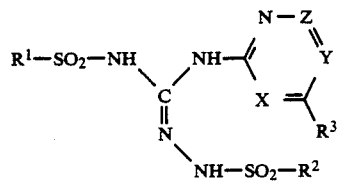  (IC)

and also for mixtures of these tautomers.

The new sulphonylaminoguanidinoazines of the general formula (I) are obtained when sulphonyl compounds of the general formula (II)

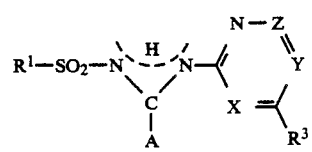  (II)

in which
$R^1$, $R^3$, X, Y and Z have the abovementioned meanings and
A stands for one of the leaving groups

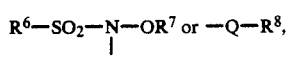

wherein
$R^6$ has the abovementioned meaning for $R^1$, but does not have to be identical with $R^1$ in each individual case,
$R^7$ stands for alkyl, alkenyl or aralkyl,
$R^8$ stands for alkyl, aralkyl or aryl and
Q stands for oxygen or sulphur, are reacted with sulphonyl hydrazides of the general formula (III)

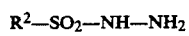  (III)

in which
$R^2$ has the abovementioned meaning,
if desired in the presence of a diluent, and the products thus obtained are converted if desired into salts by customary methods.

The new sulphonylaminoguanidinoazines of the general formula (I) are distinguished by strong herbicidal activity.

Surprisingly, the new compounds of the general formula (I) show a considerably better herbicidal action than previously known aminoguanidinoazines with an equivalent type of action.

The invention preferably related to compounds of the formula (I) in which
$R^1$ stands for the radical

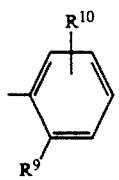

wherein
$R^9$ and $R^{10}$ are identical or different and stand for hydrogen, fluorine, chlorine, bromine, iodine, cyano, nitro, $C_1$–$C_6$-alkyl [which is optionally substituted by fluorine, chlorine, bromine, cyano, carboxyl, $C_1$–$C_4$-alkoxycarbonyl, $C_1$–$C_4$-alkylamino-carbonyl, di-($C_1$–$C_6$-alkyl)-amino-carbonyl, hydroxyl, $C_1$–$C_4$-alkoxy, formyloxy, $C_1$–$C_4$-alkylcarbonyloxy, $C_1$–$C_4$-alkoxy-carbonyloxy, $C_1$–$C_4$-alkylamino-carbonyloxy, $C_1$–$C_4$-alkylthio, $C_1$–$C_4$-alkylsulphinyl, $C_1$–$C_4$-alkylsulphonyl, di-($C_1$–$C_4$-alkyl)-aminosulphonyl, $C_3$–$C_6$-cycloalkyl or phenyl], for $C_2$–$C_6$-alkenyl [which is optionally substituted by fluorine, chlorine, bromine, cyano, $C_1$–$C_4$-alkoxycarbonyl, carboxyl or phenyl], for $C_2$–$C_6$-alkinyl [which is optionally substituted by fluorine, chlorine, bromine, cyano, $C_1$–$C_4$-alkoxy-carbonyl, carboxyl or phenyl], for $C_1$–$C_4$-alkoxy [which is optionally substituted by fluorine, chlorine, bromine, cyano, carboxyl, $C_1$–$C_4$-alkoxy-carbonyl, $C_1$–$C_4$-alkoxy, $C_1$–$C_4$-alkylthio, $C_1$–$C_4$-alkylsulphinyl or $C_1$–$C_4$-alkylsulphonyl], for $C_1$–$C_4$-alkylthio [which is optionally substituted by fluorine, chlorine, bromine, cyano, carboxyl, $C_1$–$C_4$-alkoxy-carbonyl, $C_1$–$C_4$-alkylthio, $C_1$–$C_4$-alkylsulphinyl or $C_1$–$C_4$-alkylsulphonyl], for $C_3$–$C_6$-alkenyloxy [which is optionally substituted by fluorine, chlorine, bromine, cyano or $C_1$–$C_4$-alkoxycarbonyl], for $C_2$–$C_6$-alkenylthio [which is optionally substituted by fluorine, chlorine, bromine, cyano, nitro, $C_1$–$C_3$-alkylthio or $C_1$–$C_4$-alkoxycarbonyl], $C_3$–$C_6$-alkinyloxy, $C_3$–$C_6$-alkinylthio or for the radical —S(O)$_p$—$R^{11}$,
wherein
p stands for the numbers 1 or 2 and
$R^{11}$ stands for $C_1$–$C_4$-alkyl [which is optionally substituted by fluorine, chlorine, bromine, cyano or $C_1$–$C_4$-alkoxy-carbonyl], $C_3$–$C_6$-alkenyl, $C_3$–$C_6$-alkinyl, $C_1$–$C_4$-alkoxy, $C_1$–$C_4$-alkoxy-$C_1$–$C_4$-alkylamino, $C_1$–$C_4$-alkylamino, di-($C_1$–$C_4$-alkyl)-amino or for the radical —NHOR$^{12}$,
wherein
$R^{12}$ stands for $C_1$–$C_{12}$-alkyl [which is optionally substituted by fluorine, chlorine, cyano, $C_1$–$C_4$-alkoxy, $C_1$–$C_4$-alkylthio, $C_1$–$C_4$-alkylsulphinyl, $C_1$–$C_4$-alkylsulphonyl, $C_1$–$C_4$-alkylcarbonyl, $C_1$–$C_4$-alkoxy-carbonyl, $C_1$–$C_4$-alkylamino-carbonyl or di-($C_1$–$C_4$-alkyl)-amino-carbonyl], for $C_3$–$C_3$-alkenyl [which is optionally substituted by fluorine, chlorine or bromine], $C_3$–$C_6$-alkinyl, $C_3$–$C_6$-cycloalkyl, $C_3$–$C_6$-cycloalkyl-$C_1$–$C_2$-alkyl, phenyl-$C_1$–$C_2$-alkyl [which is optionally substituted by fluorine, chlorine, nitro, cyano, $C_1$–$C_4$-alkyl, $C_1$–$C_4$-alkoxy or $C_1$–$C_4$-alkoxycarbonyl], for benzohydryl or for phenyl [which is optionally substituted by fluorine, chlorine, nitro, cyano, $C_1$–$C_4$-alkyl, trifluoromethyl, $C_1$–$C_4$-alkoxy, $C_1$–$C_2$-fluoroalkoxy, $C_1$–$C_4$-alkylthio, trifluoromethylthio or $C_1$–$C_4$-alkoxy-carbonyl], $R^9$ and $R^{10}$ furthermore stand for phenyl or phenoxy, for amino, $C_1$–$C_4$-alkylcarbonylamino, $C_1$–$C_4$-alkoxy-carbonylamino, $C_1$–$C_4$-alkylamino-carbonylamino, di-($C_1$–$C_4$-alkyl)-amino-carbonylamino, or for the radical —CO—$R^{13}$,
wherein
$R^{13}$ stands for $C_1$–$C_6$-alkyl, $C_1$–$C_6$-alkoxy, $C_3$–$C_6$-cycloalkoxy, $C_3$–$C_6$-alkenyloxy, $C_1$–$C_4$-alkylthio, $C_1$–$C_4$-alkylamino, $C_1$–$C_4$-alkoxyamino, $C_1$–$C_4$-alkoxy-$C_1$–$C_4$-alkyl-amino or di-($C_1$–$C_4$-alkyl)-amino [which are optionally substituted by fluorine and/or chlorine],
$R^9$ and $R^{10}$ furthermore stand for $C_1$–$C_4$-alkylsulphonyloxy, di-($C_1$–$C_4$-alkyl)-aminosulphonylamino, thiazolyloxy or for the radical —CH=N—$R^{14}$,
wherein
$R^{14}$ stands for $C_1$–$C_6$-alkyl which is optionally substituted by fluorine, chlorine, cyano, carboxyl, $C_1$–$C_4$-alkoxy, $C_1$–$C_4$-alkylthio, $C_1$–$C_4$-alkylsulphinyl or $C_1$–$C_4$-alkylsulphonyl, for benzyl which is optionally substituted by fluorine or chlorine, for $C_3$–$C_6$-alkenyl or $C_3$–$C_6$-alkinyl which are optionally substituted by fluorine or chlorine, for phenyl which is optionally substituted by fluorine, chlorine, bromine, $C_1$–$C_4$-alkyl, $C_1$–$C_4$-alkoxy, trifluoromethyl, trifluoromethoxy or trifluoromethylthio, for $C_1$–$C_6$-alkoxy, $C_3$–$C_6$-alkenoxy, $C_3$–$C_6$-alkinoxy or benzyloxy which are optionally substituted by fluorine and/or chlorine, for amino, $C_1$–$C_4$-alkylamino, di-($C_1$–$C_4$-alkyl)amino, phenylamino, $C_1$–$C_4$-alkyl-carbonylamino, $C_1$–$C_4$-alkoxy-carbonylamino, $C_1$–$C_4$-alkylsulphonylamino or for phenylsulphonylamino which is optionally substituted by fluorine, chlorine, bromine or methyl,
wherein in addition,
$R^1$ stands for the radical

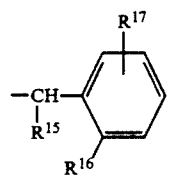

wherein
$R^{15}$ stands for hydrogen or $C_1$–$C_4$-alkyl,
$R^{16}$ and $R^{17}$ are identical or different and stand for hydrogen, fluorine, chlorine, bromine, nitro, cyano, $C_1$–$C_4$-alkyl [which is optionally substituted by fluorine and/or chlorine], $C_1$–$C_4$-alkoxy [which is optionally substituted by fluorine and/or chlorine], carboxyl, $C_1$–$C_4$-alkoxy-carbonyl, $C_1$–$C_4$-alkylsulphonyl or di-($C_1$–$C_4$-alkyl)aminosulphonyl;
wherein in addition
$R^1$ stands for the radical

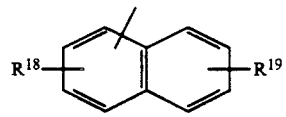

wherein
$R^{18}$ and $R^{19}$ are identical or different and stand for hydrogen, fluorine, chlorine, bromine, nitro, cyano, $C_1$–$C_4$-alkyl [which is optionally substituted by fluorine and/or chlorine] or $C_1$–$C_4$-alkoxy [which is optionally substituted by fluorine and/or chlorine];
wherein in addition $R^1$ stands for the radical

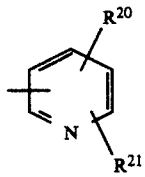

wherein
$R^{20}$ and $R^{21}$ are identical or different and stand for hydrogen, fluorine, chlorine, bromine, nitro, cyano, $C_1$–$C_4$-alkyl [which is optionally substituted by fluorine and/or chlorine], $C_1$–$C_4$-alkoxy [which is optionally substituted by fluorine and/or chlorine], for $C_1$–$C_4$-alkylthio, $C_1$–$C_4$-alkylsulphinyl or $C_1$–$C_4$-alkylsulphonyl [which are optionally substituted by fluorine and/or chlorine], and also for di-($C_1$–$C_4$-alkyl)-aminosulphonyl or $C_1$–$C_4$-alkoxy-carbonyl;
wherein in addition
$R^1$ stands for the radical

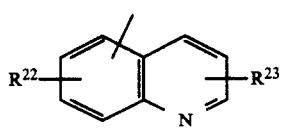

wherein
$R^{22}$ and $R^{23}$ are identical or different and stand for hydrogen, fluorine, chlorine, bromine, $C_1$–$C_4$-alkyl [which is optionally substituted by fluorine and/or bromine], $C_1$–$C_4$-alkoxy [which is optionally substituted by fluorine and/or chlorine], for $C_1$–$C_4$-alkylthio, $C_1$–$C_4$-alkylsulphinyl or $C_1$–$C_4$-alkylsulphonyl [which are optionally substituted by fluorine and/or chlorine], or for di-($C_1$–$C_4$-alkyl)-aminosulphonyl;
wherein in addition
$R^1$ stands for the radical

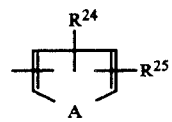

wherein
$R^{24}$ and $R^{25}$ are identical or different and stand for hydrogen, fluorine, chlorine, bromine, cyano, nitro, $C_1$–$C_4$-alkyl [which is optionally substituted by fluorine and/or chlorine], $C_1$–$C_4$-alkoxy [which is optionally substituted by fluorine and/or chlorine], $C_1$–$C_4$-alkylthio, $C_1$–$C_4$-alkylsulphinyl or $C_1$–$C_4$-alkylsulphonyl [which is optionally substituted by fluorine and/or chlorine], di-($C_1$–$C_4$-alkyl)-amino-sulphonyl or $C_1$–$C_4$-alkoxy-carbonyl, and
A stands for oxygen, sulphur or the grouping N-$Z^1$,
wherein
$Z^1$ stands for hydrogen, $C_1$–$C_4$-alkyl [which is optionally substituted by fluorine, chlorine, bromine or cyano], $C_3$–$C_6$-cycloalkyl, benzyl, phenyl [which is optionally substituted by fluorine, chlorine, bromine or nitro], $C_1$–$C_4$-alkylcarbonyl, $C_1$–$C_4$-alkoxy-carbonyl or di-($C_1$–$C_4$-alkyl)aminocarbonyl;
wherein in addition $R^1$ stands for the radical

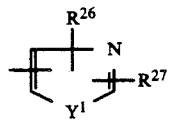

wherein
$R^{26}$ stands for hydrogen, $C_1$–$C_5$-alkyl or halogen,
$R^{27}$ stands for hydrogen or $C_1$–$C_5$-alkyl and
$Y^1$ stands for sulphur or the grouping N-$R^{28}$,
$R^{28}$ stands for hydrogen or $C_1$–$C_5$-alkyl,
wherein in addition
$R^1$ stands for the radical

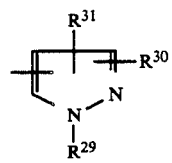

wherein
$R^{29}$ stands for hydrogen, $C_1$–$C_4$-alkyl or phenyl,
$R^{30}$ stands for hydrogen, halogen, cyano, nitro, $C_1$–$C_4$-alkyl [which is optionally substituted by fluorine and/or chlorine], $C_1$–$C_4$-alkoxy [which is optionally substituted by fluorine and/or chlorine] or $C_1$–$C_4$-alkoxy-carbonyl and
$R^{31}$ stands for hydrogen, halogen or $C_1$–$C_4$-alkyl,
wherein in addition,
$R^1$ stands for the radical

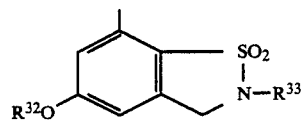

wherein
$R^{32}$ stands for $C_1$–$C_3$-alkyl and
$R^{33}$ stands for $C_1$–$C_4$-alkyl,
wherein in addition
$R^1$ stands for the radical

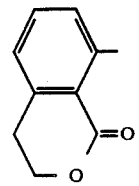

in which in addition
$R^2$ has the meaning given above as preferred for $R^1$, but does not have to be identical with $R^1$ in each individual case, and in addition can stand for di-($C_1$–$C_3$-alkyl)-amino or for $C_1$–$C_8$-alkyl which is optionally substituted by halogen,
in which in addition
$R^3$ stands for hydrogen, fluorine, chlorine, bromine, $C_1$–$C_4$-alkyl, $C_1$–$C_4$-halogenoalkylamino, $C_1$–$C_4$-alkoxy-$C_1$–$C_2$-alkyl, $C_1$–$C_4$-alkoxy, $C_1$–$C_4$-alkyl, $C_1$–$C_4$-halogenoalkylthio, diimethylamino or diethylamino, X stands for nitrogen or a —CH— grouping,
Y stands for nitrogen or a —CR$^4$—grouping,
wherein
R$^4$ stands for hydrogen, fluorine, chlorine, bromine, cyano, methyl, formyl, acetyl, methoxycarbonyl or ethoxycarbonyl and
Z stands for nitrogen or a —CR$^5$—grouping,
wherein
R$^5$ stands for hydrogen, fluorine, chlorine, bromine, C$_1$–C$_4$-alkyl, C$_1$–C$_4$-alkoxy, C$_1$–C$_4$-halogenoalkoxy, C$_1$–C$_4$alkylthio, C$_1$–C$_4$-alkylamino, dimethylamino or diethylamino, and
M stands for hydrogen or a sodium equivalent, a potassium equivalent or a calcium equivalent, an ammonium equivalent, a C$_1$–C$_6$-alkylammonium equivalent, a di-(C$_1$–C$_4$-alkyl)-ammonium or a tri-(C$_1$–C$_4$-alkyl)-ammonium equivalent,
where N'-(4,6-dimethyl-pyrimidin-2-yl)-N''-(4-methylphenylsulphonylamino)-N'''-(2-chloro-phenylsulphonyl)-guanidine is excluded.

The invention relates in particular to compounds of the formula (I) in which
R$^1$ stands for the radical

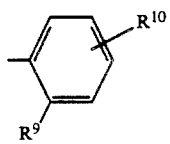

wherein
R$^9$ stands for fluorine, chlorine, bromine, methyl, trifluoromethyl, methoxy, difluoromethoxy, trifluoromethoxy, C$_1$–C$_3$-alkylthio, C$_1$–C$_3$-alkylsulphinyl, C$_1$–C$_3$-alkylsulphonyl, dimethylaminosulphonyl, diethylaminosulphonyl, N-methoxy-N-methylaminosulphonyl, phenyl, phenoxy or C$_1$–C$_3$-alkoxycarbonyl and
R$^{10}$ stands for hydrogen;
wherein in addition
R$^1$ stands for the radical

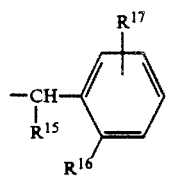

wherein
R$^{15}$ stands for hydrogen,
R16 stands for fluorine, chlorine, bromine, methyl, methoxy, ethoxy, difluoromethoxy, trifluoromethoxy, methoxycarbonyl, ethoxycarbonyl, methylsulphonyl or dimethylaminosulphonyl and
R$^{17}$ stands for hydrogen;
wherein in addition
R$^1$ stands for the radical

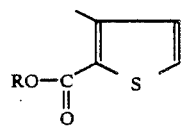

wherein
R stands for C$_1$–C$_2$-alkyl, or

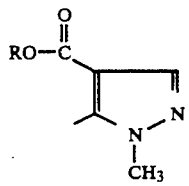

R$^1$ stands for the radical
wherein
R stands for C$_1$–C$_2$-alkyl;
in which in addition
R$^2$ stands for C$_1$–C$_4$-alkyl which is optionally substituted by fluorine or chlorine or for phenyl which is optionally substituted by fluorine, chlorine, bromine, C$_1$–C$_3$-alkyl, trifluoromethyl, chlorodifluoromethyl, methoxy, ethoxy, difluoromethoxy, trifluoromethoxy, amino, acetamido, methoxycarbonyl and/or ethoxycarbonyl,
R$^3$ stands for hydrogen, fluorine, chlorine, bromine, methyl, trifluoromethyl, methoxy, ethoxy, difluoromethoxy, methylthio, ethylthio, amino, methylamino, ethylamino, dimethylamino or diethylamino,
X stands for nitrogen or a —CH— grouping,
Y stands for nitrogen or a —CR4—grouping,
wherein
R$^4$ stands for hydrogen, fluorine, chlorine or methyl,
Z stands for nitrogen or a —CR5—grouping,
wherein
R$^5$ stands for hydrogen, fluorine, chlorine, bromine, methyl, ethyl, methoxy, ethoxy, propoxy, isopropoxy, difluoromethoxy, methylthio, ethylthio, methylamino, ethylamino, dimethylamino or diethylamino, and
M stands for hydrogen or a sodium equivalent, potassium equivalent or calcium equivalent an ammonium equivalent or a C$_1$–C$_4$-alkyl-ammonium equivalent, where N'-(4,6-dimethyl-pyrimidin-2-yl)-N''-(4-methylphenylsulphonylamino)-N'''-(2-chlorophenylsulphonyl)guanidine is excluded.

If, for example, N'-(4,6-dimethoxy-s-triazin-2-yl)-N''-methoxy-N''',N'''-bis-(2-bromo-phenylsulphonyl)-guanidine and trifluoromethanesulphonyl hydrazide are used as starting materials, then the course of the reaction in the process according to the invention can be represented by the following equation:

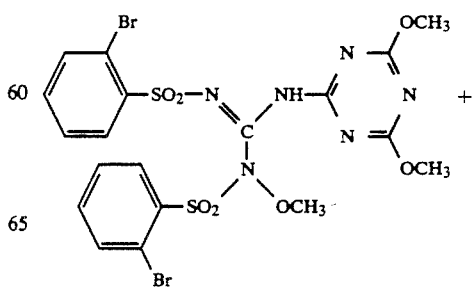

-continued

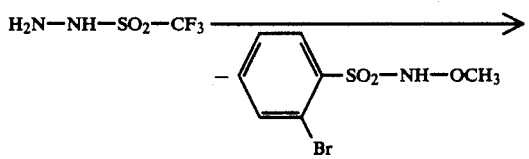

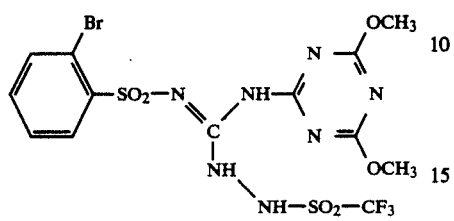

Formula (II) provides a general definition of the sulphonyl compounds to be used as starting materials in the process according to the invention. In the formula (II), $R^1$, $R^3$, X, Y and Z preferably or particularly have those meanings which have already been given above as preferred or particularly preferred for $R^1$, $R^3$, X, Y and Z in the scope of the description of the compounds of the formula (I) according to the invention and A preferably stands for one of the leaving groups $$R^6-SO_2-N(-OR^7)- \text{ or } -Q-R^8,$$

wherein
$R^6$ has the meaning given above as preferred for $R^1$, but need not be identical with $R^1$ in each individual case,
$R^7$ stands for $C_1$-$C_4$-alkyl, $C_3$-$C_4$-alkenyl or benzyl,
$R^8$ stands for $C_1$-$C_4$-alkyl, benzyl or phenyl and
Q stands for oxygen or sulphur.

In particular, A stands for the grouping $$R^6-SO_2-N(-OR^7)-,$$

wherein
$R^6$ has the meaning given above as particularly preferred for $R^1$, but does not have to be identical with $R^1$ in each individual case and
$R^7$ stands for methyl.

Examples of the starting materials of the formula (II) are shown in Table 1 below.

TABLE 1

Examples of starting materials of the formula (II)

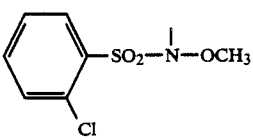

(II)

| A | $R^1$ | $R^3$ | X | Y | Z |
|---|---|---|---|---|---|
| 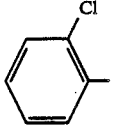 | 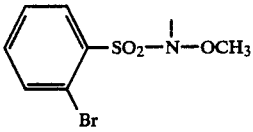 Cl | $CH_3$ | N | CH | $C-OCH_3$ |
| 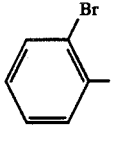 | 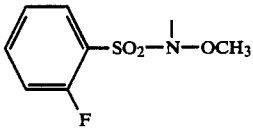 Br | $OCH_3$ | N | CH | $C-OCH_3$ |
| 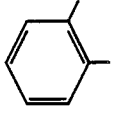 | 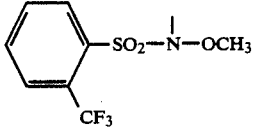 F | $OCH_3$ | N | CH | $C-OCH_3$ |
| 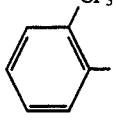 | 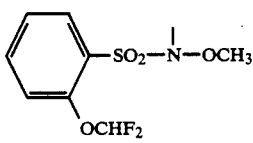 $CF_3$ | $OCH_3$ | N | CH | $C-OCH_3$ |
| 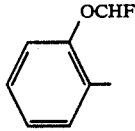 |  $OCHF_2$ | $OCH_3$ | N | CH | $C-OCH_3$ |

TABLE 1-continued
Examples of starting materials of the formula (II)
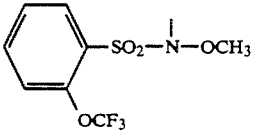
(II)
| A | R¹ | R³ | X | Y | Z |
|---|----|----|---|---|---|
| 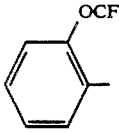 |  OCF₃ | OCH₃ | N | CH | C—OCH₃ |
| 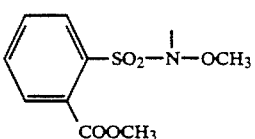 | 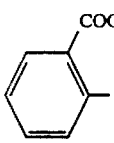 COOCH₃ | CH₃ | N | CH | C—CH₃ |
|  | 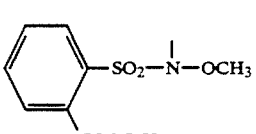 COOC₂H₅ | CH₃ | N | CH | C—CH₃ |
| 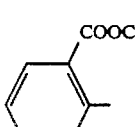 |  COOCH₃ | OCH₃ | N | CH | C—OCH₃ |
| 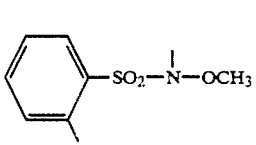 | 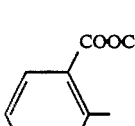 COOC₂H₅ | OCH₃ | N | CH | C—OCH₃ |
|  | 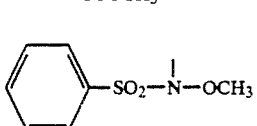 COOCH₃ | C₂H₅ | N | CH | C—OCH₃ |
| 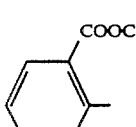 |  COOCH₃ | C₂H₅ | N | CH | C—OCH₃ |
| 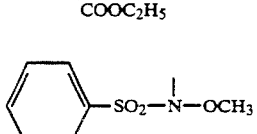 | 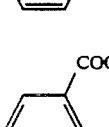 COOCH₃ | OCH₃ | N | CH | C—Cl |
|  | 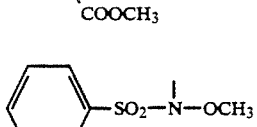 COOC₂H₅ | OCH₃ | N | CH | C—Cl |

TABLE 1-continued

Examples of starting materials of the formula (II)

$$R^1-SO_2-N\overset{H}{\underset{\underset{A}{C}}{-}}N=\overset{N-Z}{\underset{\underset{R^3}{\parallel}}{C-Y}}$$
(II)

| A | R¹ | R³ | X | Y | Z |
|---|---|---|---|---|---|
| 2-OCF₃-phenyl-SO₂-N(OCH₃)- | 2-OCF₃-phenyl | OCH₃ | N | CH | C—Cl |
| 2-OCHF₂-phenyl-SO₂-N(OCH₃)- | 2-OCHF₂-phenyl | OCH₃ | N | CH | C—Cl |
| 2-SO₂CH₃-phenyl-SO₂-N(OCH₃)- | 2-SO₂CH₃-phenyl | H | N | CH | C—CH₃ |
| 2-SO₂N(CH₃)₂-phenyl-SO₂-N(OCH₃)- | 2-SO₂N(CH₃)₂-phenyl | CH₃ | N | CH | C—OCH₃ |
| 2-CH₃-phenyl-SO₂-N(OCH₃)- | 2-CH₃-phenyl | OCH₃ | N | CH | C—OCH₃ |
| 2-OCH₃-phenyl-SO₂-N(OCH₃)- | 2-OCH₃-phenyl | CH₃ | N | CH | C—OCH₃ |
| 2-SCH₃-phenyl-SO₂-N(OCH₃)- | 2-SCH₃-phenyl | OCH₃ | N | CH | C—OCH₃ |
| 2-[SO₂N(CH₃)(OCH₃)]-phenyl-SO₂-N(OCH₃)- | 2-[SO₂N(CH₃)(OCH₃)]-phenyl | OCH₃ | N | CH | C—OCH₃ |
| 2-COOCH₃-phenyl-SO₂-N(OCH₃)- | 2-COOCH₃-phenyl | CH₃ | N | CH | C—OC₂H₅ |

TABLE 1-continued
Examples of starting materials of the formula (II)
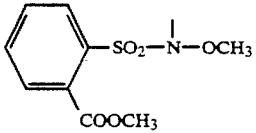
| A | R¹ | R³ | X | Y | Z |
|---|---|---|---|---|---|
| 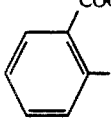 | 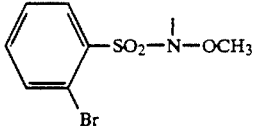 | $OCHF_2$ | N | CH | $C-CH_3$ |
| 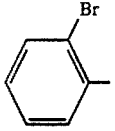 | 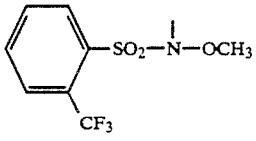 | $CH_3$ | N | CH | $C-SCH_3$ |
| 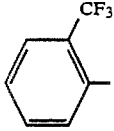 | 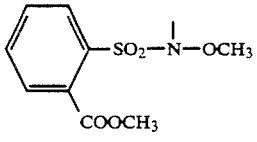 | $CH_3$ | N | CH | $C-N(CH_3)_2$ |
| 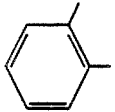 | 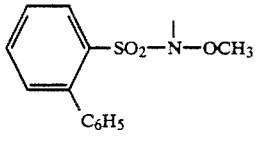 | $OCHF_2$ | N | CH | $C-OCHF_2$ |
| 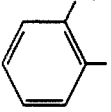 | 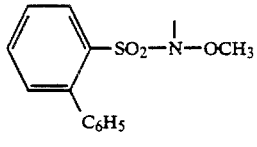 | $OCH_3$ | N | CH | $C-OCH_3$ |
| 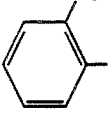 | 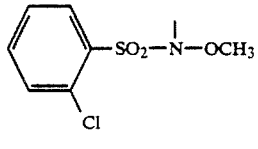 | $OCH_3$ | N | N | $C-OCH_3$ |
| 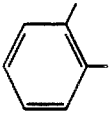 | 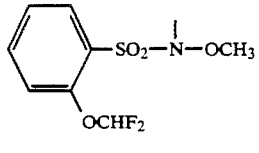 | $CH_3$ | N | N | $C-OCH_3$ |
| 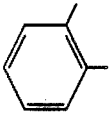 | 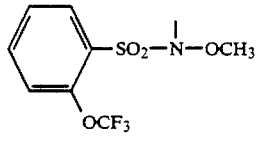 | $OCH_3$ | N | N | $C-OCH_3$ |
| 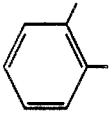 | | $OCH_3$ | N | N | $C-OCH_3$ |

TABLE 1-continued

Examples of starting materials of the formula (II)

$$R^1-SO_2-N\underset{H}{\overset{}{-}}\underset{\underset{A}{C}}{\overset{}{-}}N=\underset{\underset{R^3}{\overset{}{-}}}{\overset{N-Z}{\underset{X}{\overset{}{\diagdown}}}\overset{}{\diagup}}Y$$ (II)

| A | R¹ | R³ | X | Y | Z |
|---|---|---|---|---|---|
| 2-(COOCH₃)-C₆H₄-SO₂-N(OCH₃)- | 2-(COOCH₃)-C₆H₄- | CH₃ | N | N | C—OCH₃ |
| 2-(COOCH₃)-C₆H₄-SO₂-N(OCH₃)- | 2-(COOCH₃)-C₆H₄- | OCH₃ | N | N | C—OCH₃ |
| 2-Br-C₆H₄-SO₂-N(OCH₃)- | 2-Br-C₆H₄- | CH₃ | N | N | C—CH₃ |
| 2-CF₃-C₆H₄-SO₂-N(OCH₃)- | 2-CF₃-C₆H₄- | CH₃ | N | N | C—Cl |
| 2-(COOC₂H₅)-C₆H₄-SO₂-N(OCH₃)- | 2-(COOC₂H₅)-C₆H₄- | OCH₃ | N | N | C—OCH₃ |
| 2-F-C₆H₄-SO₂-N(OCH₃)- | 2-F-C₆H₄- | OCH₃ | N | N | C—OCH₃ |
| 2-(SC₂H₅)-C₆H₄-SO₂-N(OCH₃)- | 2-(SC₂H₅)-C₆H₄- | OCH₃ | N | N | C—OCH₃ |
| 2-(COOCH₃)-C₆H₄-CH₂-SO₂-N(OCH₃)- | 2-(COOCH₃)-C₆H₄-CH₂- | OCH₃ | N | CH | C—OCH₃ |
| 2-(OCF₃)-C₆H₄-CH₂-SO₂-N(OCH₃)- | 2-(OCF₃)-C₆H₄-CH₂- | OCH₃ | N | CH | C—OCH₃ |

TABLE 1-continued

Examples of starting materials of the formula (II)

$$R^1-SO_2-N\underset{H}{\overset{}{-}}\underset{\underset{A}{|}}{C}=N-\underset{\underset{R^3}{|}}{C}\overset{N-Z}{\underset{X}{\diagdown}}\!\!\!\!\!\!\!\!\!\!\!\!\!\!\overset{\diagup}{\diagdown}Y \qquad (II)$$

| A | $R^1$ | $R^3$ | X | Y | Z |
|---|---|---|---|---|---|
| —OC$_6$H$_5$ | 2-Cl-C$_6$H$_4$ | CH$_3$ | N | CH | C—CH$_3$ |
| —OCH$_3$ | 2-Cl-C$_6$H$_4$ | CH$_3$ | N | CH | C—OCH$_3$ |
| —SCH$_3$ | 2-Cl-C$_6$H$_4$ | OCH$_3$ | N | CH | C—OCH$_3$ |
| —SC$_6$H$_5$ | 2-Cl-C$_6$H$_4$ | OCH$_3$ | N | CH | C—OCH$_3$ |
| 3-(SO$_2$—N(OCH$_3$)—)-2-(COOCH$_3$)-thienyl | | 3-methyl-2-(COOCH$_3$)-thienyl CH$_3$ | N | N | C—OCH$_3$ |
| 4-(COOCH$_3$)-5-(SO$_2$—N(OCH$_3$)—)-1-methyl-pyrazol-3-yl | | 4-(COOCH$_3$)-1,3-dimethyl-pyrazol-5-yl OCH$_3$ | N | CH | C—OCH$_3$ |
| 2-(COOCH$_3$)-6-(SO$_2$—N(OCH$_3$)—)-phenyl | | 4-(COOC$_2$H$_5$)-1,3-dimethyl-pyrazol-5-yl OCH$_3$ | N | CH | C—OCH$_3$ |

The starting materials of the formula (II) are known and/or can be prepared by processes which are known per se (compare EP-A 121,082, EP-A 172,957, EP-A 173,321, EP-A 173,956, EP-A 224,078, EP-A 5,986 and EP-A 24,215).

Formula (III) provides a general definition of the sulphonyl hydrazides to be used in addition as starting materials in the process according to the invention. In formula (III), $R^2$ preferably or particularly has those meanings which have already been given above as preferred or as particularly preferred for $R^2$ in the scope of the description of the compounds of the formula (I) according to the invention.

Examples of the compounds of the formula (III) which may be mentioned are: methane-, ethane-, propane- and butane-sulphonyl hydrazide, trifluorome- thane-, perfluorobutane-, chloromethane- and 2-chloroethane-sulphonyl hydrazide, benzenesulphonyl hydrazide, 2-fluoro-, 4-fluoro-, 2-chloro-, 4-chloro-, 2-bromo-, 4-bromo-, 2-methyl-, 4-methyl-, 2-trifluoromethyl-, 3-chlorodifluoromethyl-, 2-methoxy-, 4-methoxy-, 2-ethoxy-, 4-ethoxy-, 2-difluoromethoxy-, 2-trifluoromethoxy-, 4-trifluoromethoxy-, 3-trifluoromethoxy-, 2-methoxycarbonyl-, 4-methoxycarbonyl-, 2-ethoxycarbonyl-, 4-ethoxycarbonylbenzenesulphonyl hydrazide and dimethylsulphamoyl hydrazine.

The starting materials of the formula (III) are known and/or can be prepared by processes which are known per se (compare Org. Synth. 40 (1960), 93–95).

The process according to the invention for the preparation of the new sulphonylaminoguanidinoazines of the formula (I) is preferably carried out using diluents. Possible diluents here are preferably water and/or polar organic solvents, such as methanol, ethanol, isopropanol, butanol, isobutanol, sec-butanol, tert-butanol, glycol dimethyl ether, diglycol dimethyl ether, tetrahydrofuran, dioxane, methyl acetate, ethyl acetate, acetonitrile, propionitrile, dimethylformamide, dimethylacetamide, N-methylpyrrolidone, dimethyl sulphoxide and tetramethylenesulphone.

The reaction temperatures can be varied within a relatively wide range when carrying out the process according to the invention. In general, the reaction is carried out at temperatures between 0° C. and 150° C., preferably at temperatures between 10° C. and 100° C.

For carrying out the process according to the invention, between 1 and 5 mols, preferably between 1 and 3 mols, of sulphonyl hydrazide of the formula (III) are generally employed per mol of sulphonyl compound of the formula (II).

In general, the reaction components are combined at room temperature or with ice cooling and the reaction mixture is stirred until completion of the reaction, if necessary at elevated temperature. The products of the formula (I) are generally precipitated as crystals after cooling and can be isolated by filtering off with suction.

For conversion into salts, the compounds of the formula (I) in which M stands for hydrogen are stirred with suitable metal compounds, such as, for example, sodium hydroxide or potassium hydroxide, sodium methylate or potassium methylate, or sodium ethylate or potassium ethylate or with suitable amines, such as, for example, isopropylamine, in suitable diluents, such as, for example, water, methanol or ethanol. The salts can then be isolated - if appropriate after concentration, as crystalline products.

The active compounds according to the invention can be used as defoliants, desiccants, agents for destroying broad-leaved plants and, especially, as weedkillers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants: Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea. Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita. Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera. Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The new active compounds are suitable for selectively combating monocotyledon and dicotyledon weeds using the pre-emergence and the post-emergence methods, in particular in monocotyledon crops, particularly also paddy rice.

On application of the new active compounds, defoliant action and activity against rice diseases, such as *Pyricularia oryzae*, was also observed.

The active compounds can be converted into the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkyl naphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silicic acid, alumina and silicates, as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkylsulphonates, alkylsulphates, arylsulphonates as well as albumin hydrolysation products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention, as such or in the form of their formulations, can also be used, for combating weeds, as mixtures with known herbicides, finished formulations or tank mixes being possible.

Possible components for the mixtures are known herbicides, such as, for example, 1-amino-6-ethylthio-3-(2,2-dimethylpropyl)-1,3,5-triazine-2,4(1H,3H)-dione or N-(2-benzothiazolyl)-N,N'-dimethylurea for combating weeds in cereals; 4-amino-3-methyl-6-phenyl-1,2,4-triazin-5(4H)-one for combating weeds in sugar beets, and 4-amino-6-(1,1-dimethylethyl)-3-methylthio-1,2,4-triazin-5(4H)-one for combating weeds in soy beans, and furthermore also 2,4-dichlorophenoxyacetic acid; 4-(2,4-dichlorophenoxy)-butyric acid; 2,4-dichlorophenoxypropionic acid; methyl 2-[[[[[(4,6-dimethoxypyrimidin-2-yl)-amino]-carbonyl]-amino]-sulphonyl]-methyl]-benzoate; 3-isopropyl-2,1,3-benzothiadiazin-4-one 2,2-dioxide; methyl 5-(2,4-dichlorophenoxy)-2-nitrobenzoate; 3,5-dibromo-4-hydroxy-benzonitrile; N-(butoxymethyl)-2-chloro-N-(2,6-diethylphenyl)-acetamide; 2-chloro-N-{[(4-methoxy-6-methyl-1,3,5-triazin-2-yl)-amino]carbonyl}-benzenesulphonamide; N,N-dimethyl-N'-(3-chloro-4-methylphenyl)-urea; 2-[4-(2,4-dichlorophenoxy)-phenoxy]propionic acid, its methyl or its ethyl ester; 3,6-dichloro-2-pyridinecarboxylic acid; 4-amino-6-t-butyl-3-ethylthio-1,2,4-triazin-5(4H)-one; 2-{4-[(6-chloro-2-benzoxazolyl)oxy]-phenoxy}-propanoic acid, its methyl or its ethyl ester; trimethylsilylmethyl 2-[4-(3,5-dichloropyrid-2-yloxy)-phenoxy]-propionate; 2-(4,5-dihydro-4-methyl-4-isopropyl-5-oxo-1H-imidazol-2-yl)-pyridine-3-carboxylic acid; 3,5-diiodo-4-hydroxybenzonitrile; N,N-dimethyl-N'-(4-isopropylphenyl)-urea; (2-methyl-4-chlorophenoxy)-acetic acid; (4-chloro-2-methylphenoxy)-propionic acid; 2-{[[((4-methoxy-6-methyl-1,3,5-triazin-2-yl)-amino)-carbonyl]-amino]sulphonyl}-benzoic acid or its methyl ester; S-ethyl N,N-hexamethylene-thiocarbamate; 4-(di-n-propylamino)-3,5-dinitrobenzenesulphonamide; N-(1-ethylpropyl)-3,4-dimethyl- 2,6-dinitroaniline; α-chloro-2', 6'-diethyl-N-(2-propoxyethyl)-acetanilide; 2-chloro-N-isopropylacetanilide; 4-ethylamino-2-t-butylamino-6-methylthio-s-triazine; methyl 3-[[[[(4-methoxy-6-methyl-1,3,5-triazin-2-yl)-amino]-carbonyl]-amino]-sulphonyl]-thiophene-2-carboxylate; N,N-diisopropyl-S-(2,3,3-trichloroallyl)-thiocarbamate and 3,5,6-trichloro-2-pyridyloxyacetic acid. Surprisingly, some mixtures also show a synergistic action.

Mixtures with other known active compounds, such as fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants.

They can also be incorporated into the soil before sowing.

The amount of active compound used can vary within a relatively wide range. It depends essentially on the nature of the desired effect. In general, the amounts used are between 0.01 and 15 kg of active compound per hectare of soil surface, preferably between 0.05 and 10 kg per ha.

The preparation and use of the active compounds according to the invention can be seen from the following examples.

PREPARATION EXAMPLES

EXAMPLE 1

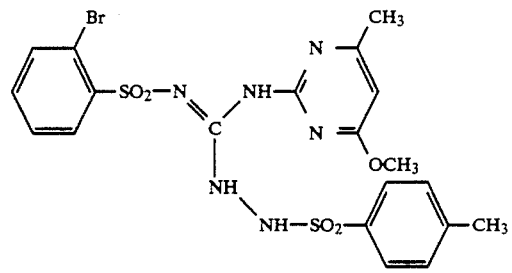

A mixture of 6.5 g (0.01 mol) of N'-(4-methoxy-6-methyl-pyrimidin-2-yl)-N''-methoxy-N'',N'''-bis-(2-bromophenylsulphonyl)-guanidine, 5.6 g (0.03 mol) of p-toluenesulphonyl hydrazide, 30 ml of ethanol and 10 ml of water is heated to boiling under reflux for 60 minutes and then stirred for 20 hours at 20° C.. The precipitated crystalline product is isolated by filtering with suction.

3.1 g (51% of theory) of N'-(4-methoxy-6-methyl-pyrimidin-2-yl)-N''-(4-methyl-phenylsulphonylamino)-N'''-(2-bromo-phenylsulphonyl)-guanidine of melting point 156° C. are obtained.

The compounds of the formula (I) shown in Table 2 below can be prepared analogously to Example 1 and corresponding to the general description of the process according to the invention.

TABLE 2
Examples of compounds of the formula (I)
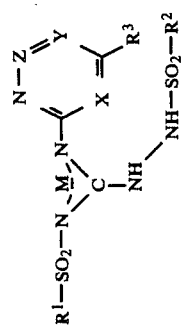
| Example No. | M | $R^1$ | $R^2$ | $R^3$ | X | Y | Z | Melting point (°C.) |
|---|---|---|---|---|---|---|---|---|
| 2 | H | 2-COOCH$_3$-C$_6$H$_4$ | 2-COOCH$_3$-C$_6$H$_4$ | CH$_3$ | N | CH | C—CH$_3$ | 153 |
| 3 | H | 2-OCF$_3$-C$_6$H$_4$ | 4-CH$_3$-C$_6$H$_4$ | OCH$_3$ | N | CH | C—OCH$_3$ | 163 |
| 4 | H | 2-OCF$_3$-C$_6$H$_4$ | C$_6$H$_5$ | OCH$_3$ | N | CH | C—OCH$_3$ | 110 |
| 5 | H | 2-COOCH$_3$-C$_6$H$_4$ | C$_6$H$_5$ | OCH$_3$ | N | CH | C—OCH$_3$ | 174 |
| 6 | H | 2-COOCH$_3$-C$_6$H$_4$ | 4-CH$_3$-C$_6$H$_4$ | OCH$_3$ | N | CH | C—OCH$_3$ | 177 |

TABLE 2-continued
Examples of compounds of the formula (I)
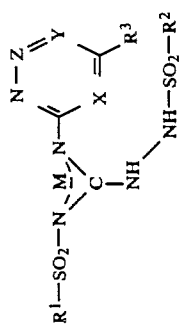
| Example No. | M | R¹ | R² | R³ | X | Y | Z | Melting point (°C.) |
|---|---|---|---|---|---|---|---|---|
| 7 | H | 2-COOCH₃, 6-CH₂-phenyl | 4-CH₃-phenyl | OCH₃ | N | CH | C—OCH₃ | 166 |
| 8 | H | 2-Br-phenyl | 4-CH₃-phenyl | OCH₃ | N | CH | C—OCH₃ | 102 |
| 9 | H | 2-OCF₃-phenyl | CH₃ | OCH₃ | N | CH | C—OCH₃ | 174 |
| 10 | H | 2-COOCH₃, 6-CH₂-phenyl | CH₃ | OCH₃ | N | CH | C—OCH₃ | 87 |
| 11 | H | 2-COOCH₃-phenyl | CH₃ | OCH₃ | N | CH | C—OCH₃ | 184 |

TABLE 2-continued

Examples of compounds of the formula (I)

| Example No. | M | R$^1$ | R$^2$ | R$^3$ | X | Y | Z | Melting point (°C.) |
|---|---|---|---|---|---|---|---|---|
| 12 | H | 2-(COOCH$_3$)-C$_6$H$_4$-CH$_2$- | 4-Cl-2-CF$_3$-C$_6$H$_3$- | OCH$_3$ | N | CH | C—OCH$_3$ | 113 |
| 13 | H | 2-(COOCH$_3$)-C$_6$H$_4$-CH$_2$- | C$_3$H$_7$ | OCH$_3$ | N | CH | C—OCH$_3$ | 155 |
| 14 | H | 2-(COOCH$_3$)-C$_6$H$_4$-CH$_2$- | 3-(CF$_2$Cl)-C$_6$H$_4$- | OCH$_3$ | N | CH | C—OCH$_3$ | 147 |
| 15 | H | 2-(COOCH$_3$)-C$_6$H$_4$-CH$_2$- | 4-OCH$_3$-C$_6$H$_4$- | OCH$_3$ | N | CH | C—OCH$_3$ | 151 |
| 16 | Na | 2-(COOCH$_3$)-C$_6$H$_4$-CH$_2$- | 4-CH$_3$-C$_6$H$_4$- | OCH$_3$ | N | CH | C—OCH$_3$ | |

TABLE 2-continued
Examples of compounds of the formula (I)
| Example No. | M | R¹ | R² | R³ | X | Y | Z | Melting point (°C.) |
|---|---|---|---|---|---|---|---|---|
| 17 | K | 2-(COOCH₃)-benzyl (CH₂-C₆H₄-COOCH₃) | 4-CH₃-C₆H₄ | OCH₃ | N | CH | C—OCH₃ | |
| 18 | H | 2-(COOCH₃)-benzyl | C₆H₅ | OCH₃ | N | CH | C—OCH₃ | |
| 19 | H | 2-(COOC₂H₅)-phenyl | C₆H₅ | OCH₃ | N | CH | C—OCH₃ | |
| 20 | H | 2-(OCF₃)-benzyl | C₆H₅ | OCH₃ | N | CH | C—OCH₃ | |
| 21 | H | 2-F-C₆H₄ | 4-CH₃-C₆H₄ | CH₃ | N | CH | C—OCH₃ | 154 |

TABLE 2-continued

Examples of compounds of the formula (I)

$$R^1-SO_2-N(M)-C(=N-NH-SO_2-R^2)-NH-\underset{X}{\overset{N-Z}{\underset{Y}{\rightleftarrows}}}R^3 \quad (I)$$

| Example No. | M | R¹ | R² | R³ | X | Y | Z | Melting point (°C.) |
|---|---|---|---|---|---|---|---|---|
| 22 | H | 2-OCF₃-phenyl | 4-CH₃-phenyl | CH₃ | N | CH | C—OCH₃ | 179 |
| 23 | H₃NCH(CH₃)₂ | 2-OCF₃-phenyl | 4-CH₃-phenyl | CH₃ | N | CH | C—OCH₃ | 84 |
| 24 | K | 2-OCF₃-phenyl | 4-CH₃-phenyl | CH₃ | N | CH | C—OCH₃ | 127 |
| 25 | H | 2-OCF₃-phenyl | 4-CH₃-phenyl | CH₃ | N | CH | C—OC₂H₅ | 155 |
| 26 | H | 2-OCF₃-phenyl | CH₃ | CH₃ | N | CH | C—OCH₃ | 178 |

TABLE 2-continued
Examples of compounds of the formula (I)
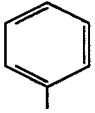
| Example No. | M | R¹ | R² | R³ | X | Y | Z | Melting point (°C.) |
|---|---|---|---|---|---|---|---|---|
| 27 | H | 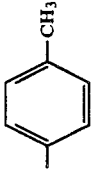 | 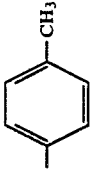 | $CH_3$ | N | CH | C—$OCH_3$ | 182 |
| 28 | H | 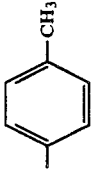 | 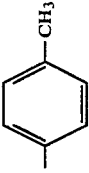 | $CH_3$ | N | CH | C—$OC_2H_5$ | |
| 29 | H | 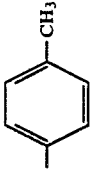 | 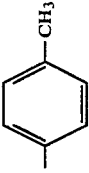 | $C_2H_5$ | N | CH | C—$OCH_3$ | 173 |
| 30 | H | 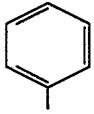 | 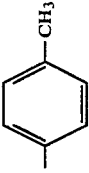 | $CH_3$ | N | CH | C—$OCH_3$ | |
| 31 | H | 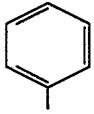 | 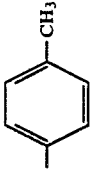 | $CH_3$ | N | CH | C—$OCH_3$ | |

TABLE 2-continued

Examples of compounds of the formula (I)

$$R^1-SO_2-N=\underset{NH}{\overset{M}{\underset{|}{C}}}-N\underset{X}{\overset{N-Z}{\underset{\|}{\underset{|}{C}}}}\underset{R^3}{\overset{Y}{\underset{|}{C}}}$$
$$\phantom{xxxxxxxxx}|\phantom{xxxx}NH-SO_2-R^2$$ (I)

| Example No. | M | R¹ | R² | R³ | X | Y | Z | Melting point (°C.) |
|---|---|---|---|---|---|---|---|---|
| 32 | H | 2-COOCH₃-phenyl | CH₃ | CH₃ | N | CH | C—OCH₃ | |
| 33 | H | 2-COOC₂H₅-phenyl | CH₃ | CH₃ | N | CH | C—OCH₃ | |
| 34 | H | 2-COOC₂H₅-phenyl | phenyl | CH₃ | N | CH | C—OCH₃ | |
| 35 | H | 2-COOCH₃-phenyl | phenyl | CH₃ | N | N | C—OCH₃ | 183 |
| 36 | H | 2-COOCH₃-phenyl | CH₃ | CH₃ | N | N | C—OCH₃ | |

TABLE 2-continued

Examples of compounds of the formula (I)

$$R^1-SO_2-N(M)-C(=N-N=Y-Z / X-R^3)-NH-NH-SO_2-R^2$$

| Example No. | M | R¹ | R² | R³ | X | Y | Z | Melting point (°C.) |
|---|---|---|---|---|---|---|---|---|
| 37 | H | 2-(COOC₂H₅)-C₆H₄ | C₆H₅ | OCH₃ | N | N | C—OCH₃ | |
| 38 | H | 2-(COOC₂H₅)-C₆H₄ | CH₃ | OCH₃ | N | N | C—OCH₃ | |
| 39 | H | 2-(OCF₃)-C₆H₄ | CH₃ | OCH₃ | N | N | C—OCH₃ | |
| 40 | H | 2-Cl-C₆H₄ | C₆H₅ | OCH₃ | N | N | C—OCH₃ | |
| 41 | H | 2-Br-C₆H₄ | CH₃ | OCH₃ | N | N | C—OCH₃ | |

TABLE 2-continued

Examples of compounds of the formula (I)

$$R^1-SO_2-N-\underset{NH}{\overset{M}{N}}\underset{C}{\overset{N-Z}{\diagdown}}\overset{N-Z}{\underset{X}{\diagup}}\overset{R^3}{\underset{NH-SO_2-R^2}{}}\quad (I)$$

| Example No. | M | R¹ | R² | R³ | X | Y | Z | Melting point (°C.) |
|---|---|---|---|---|---|---|---|---|
| 42 | H | 2-COOC₂H₅-phenyl | phenyl | CH₃ | N | N | C—CH₃ | |
| 43 | H | 2-F-phenyl | CH₃ | OCH₃ | N | N | C—OCH₃ | |
| 44 | H | 2-CF₃-phenyl | phenyl | OCH₃ | N | N | C—OCH₃ | |
| 45 | H | 2-OCHF₂-phenyl | CH₃ | OCH₃ | N | N | C—OCH₃ | |
| 46 | H | 2-Cl-phenyl | 4-CH₃-phenyl | CH₃ | N | N | C—OCH₃ | |

TABLE 2-continued

Examples of compounds of the formula (I)

$$R^1-SO_2-N-\underset{M}{\overset{N-Z}{\underset{NH}{C}}}\underset{NH-SO_2-R^2}{\overset{Y}{\underset{X}{\rightleftharpoons}}}R^3 \quad (I)$$

| Example No. | M | R¹ | R² | R³ | X | Y | Z | Melting point (°C.) |
|---|---|---|---|---|---|---|---|---|
| 47 | H | 2-COOCH₃-phenyl | phenyl | CH₃ | N | N | C—OCH₃ | |
| 48 | H | 2-COOCH₃-phenyl | phenyl | OCH₃ | N | N | C—OCH₃ | |
| 49 | H | 2-COOCH₃-phenyl | phenyl | C₂H₅ | N | N | C—OCH₃ | |
| 50 | H | 2-COOCH₃-phenyl | phenyl | CH₃ | N | N | C—OC₂H₅ | |
| 51 | H | 2-COOCH₃-benzyl | 4-(NH—CO—CH₃)-phenyl | OCH₃ | N | CH | C—OCH₃ | 223 |

TABLE 2-continued

Examples of compounds of the formula (I)

$$R^1-SO_2-N-\underset{NH}{\overset{M}{\underset{|}{C}}}-N \underset{X}{\overset{N-Z}{\underset{Y}{\diagdown}}} R^3$$
$$NH-SO_2-R^2 \quad (I)$$

| Example No. | M | R¹ | R² | R³ | X | Y | Z | Melting point (°C.) |
|---|---|---|---|---|---|---|---|---|
| 52 | H | 2-(COOCH₃)-benzyl (CH₂-C₆H₄-COOCH₃) | 2,4,6-trimethylphenyl | OCH₃ | N | CH | C—OCH₃ | 100 |
| 53 | H | 2-(COOCH₃)-benzyl (CH₂-C₆H₄-COOCH₃) | 4-NH₂-phenyl | OCH₃ | N | CH | C—OCH₃ | 218 |
| 54 | H | 4-COOC₂H₅-3-methyl-1-methylpyrazol-5-yl | 4-methylphenyl | OCH₃ | N | CH | C—OCH₃ | 112 |
| 55 | H | 3-methyl-2-COOCH₃-thien-... | phenyl | CH₃ | N | N | C—OCH₃ | |
| 56 | H | 3-methyl-2-COOCH₃-thien-... | 4-methylphenyl | OCH₃ | N | N | C—OCH₃ | |

TABLE 2-continued

Examples of compounds of the formula (I)

$$R^1-SO_2-N(M)-C(=NH)-NH-SO_2-R^2 \text{ ; heterocycle with } X, Y, Z, N-N, R^3 \quad (I)$$

| Example No. | M | R¹ | R² | R³ | X | Y | Z | Melting point (°C.) |
|---|---|---|---|---|---|---|---|---|
| 57 | H | 1-methyl-4-COOCH₃-pyrazol-5-yl | phenyl | OCH₃ | N | N | C—OCH₃ | |
| 58 | H | 2-COOCH₃-phenyl | phenyl | CH₃ | N | CH | C—CH₃ | |
| 59 | H | 2-COOC₂H₅-phenyl | phenyl | CH₃ | N | CH | C—CH₃ | |
| 60 | H | 3-methyl-2-COOCH₃-thien-yl | phenyl | OCH₃ | N | CH | C—OCH₃ | |
| 61 | H | 2-OCF₃-phenyl | phenyl | CH₃ | N | CH | C—CH₃ | |

TABLE 2-continued
Examples of compounds of the formula (I)

$$R^1-SO_2-N\underset{M}{\overset{N}{=}}\underset{NH}{\overset{}{C}}-NH-SO_2-R^2 \quad \underset{X}{\overset{N-Z}{\underset{}{\bigvee}}}\overset{R^3}{\underset{Y}{}} \quad (I)$$

| Example No. | M | R¹ | R² | R³ | X | Y | Z | Melting point (°C.) |
|---|---|---|---|---|---|---|---|---|
| 62 | H | (pyrazole with COOC₂H₅, CH₃, N-CH₃) | phenyl | OCH₃ | N | CH | C—OCH₃ | |
| 63 | H | (pyrazole with COOC₂H₅, CH₃, N-CH₃) | phenyl | OCH₃ | N | N | C—OCH₃ | |
| 64 | H | 2-Br-phenyl | phenyl | OCH₃ | N | N | C—OCH₃ | |
| 65 | H | 2-CF₃-phenyl | phenyl | CH₃ | N | CH | C—CH₃ | |
| 66 | H | 2-F-phenyl | phenyl | CH₃ | N | CH | C—CH₃ | |

TABLE 2-continued
Examples of compounds of the formula (I)
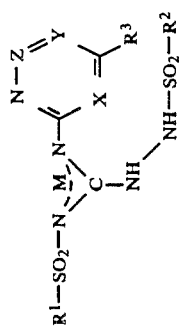
| Example No. | M | $R^1$ | $R^2$ | $R^3$ | X | Y | Z | Melting point (°C.) |
|---|---|---|---|---|---|---|---|---|
| 67 | H | 2-OCF₃-phenyl | phenyl | CH₃ | N | CH | C—CH₃ | |
| 68 | H | 2-F-phenyl | phenyl | OCH₃ | N | CH | C—OCH₃ | |
| 69 | H | 2-Cl-phenyl | phenyl | OCH₃ | N | CH | C—OCH₃ | |
| 70 | H | 2-COOC₂H₅-phenyl | phenyl | OCH₃ | N | CH | C—Cl | |
| 71 | H | 2-COOC₂H₅-phenyl | —C₃H₇-n | OCH₃ | N | CH | C—Cl | |

TABLE 2-continued
Examples of compounds of the formula (I)
| Example No. | M | R¹ | R² | R³ | X | Y | Z | Melting point (°C.) |
|---|---|---|---|---|---|---|---|---|
| 72 | H | COOCH₃-C₆H₄-CH₂- | N(CH₃)₂ | OCH₃ | N | CH | C—OCH₃ | 158 |
| 73 | H | COOCH₃-C₆H₄-CH₂- | C₆H₅ | OCH₃ | N | CH | C—OCH₃ | |
| 74 | H | COOC₂H₅-pyrazole-CH₃ | CH₃ | OCH₃ | N | CH | C—OCH₃ | |
| 75 | H | COOC₂H₅-pyrazole-CH₃ | —C₃H₇-n | OCH₃ | N | CH | C—OCH₃ | |
| 76 | H | COOC₂H₅-pyrazole-CH₃ | OCF₃-C₆H₄-CH₂- | OCH₃ | N | CH | C—OCH₃ | |

TABLE 2-continued
Examples of compounds of the formula (I)
$$R^1-SO_2-N-\underset{M}{\overset{N}{C}}\overset{N-N}{\underset{NH}{=}}\overset{Y}{\underset{X}{\overset{}{\bigvee}}}R^3 \quad NH-SO_2-R^2 \quad (I)$$
| Example No. | M | $R^1$ | $R^2$ | $R^3$ | X | Y | Z | Melting point (°C.) |
|---|---|---|---|---|---|---|---|---|
| 77 | H | 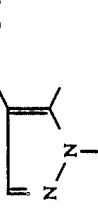 | $N(CH_3)_2$ | $OCH_3$ | N | CH | C—$OCH_3$ | |
| 78 | H | 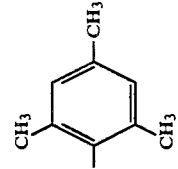 |  | $OCH_3$ | N | CH | C—Cl | |
| 79 | H |  | (p-tolyl) | $CH_3$ | N | N | C—$OCH_3$ | |
| 80 | H | (COOC2H5, OCHF2-phenyl) | (phenyl) | $OCH_3$ | N | CH | C—$OCH_3$ | |

TABLE 2-continued

Examples of compounds of the formula (I)

$$R^1-SO_2-N \overset{M=N}{\underset{NH}{\bigvee}} \overset{N-Z}{\underset{C}{\bigvee}} \overset{Y}{\underset{X}{\bigvee}} R^3 \atop NH-SO_2-R^2 \quad (I)$$

| Example No. | M | R¹ | R² | R³ | X | Y | Z | Melting point (°C.) |
|---|---|---|---|---|---|---|---|---|
| 81 | H | 2-COOCH₃-phenyl | 4-CH₃-phenyl | OCHF₂ | N | CH | C—OCHF₂ | |
| 82 | H | 2-COOCH₃-phenyl | 4-CH₃-phenyl | OCH₃ | N | CH | CH(OCH₃)₂ | |
| 83 | H | 2-SO₂N(C₄H₉-n)-5-CH₃O-phenyl (with CH₂) | 4-CH₃-phenyl | OCH₃ | N | CH | C—OCH₃ | |
| 84 | H | 3-CF₃-2-pyridyl | 4-CH₃-phenyl | OCH₃ | N | CH | C—OCH₃ | |
| 85 | H | 2-(thiazol-2-yloxy)phenyl | phenyl | OCH₃ | N | N | C—OCH₃ | |

TABLE 2-continued
Examples of compounds of the formula (I)
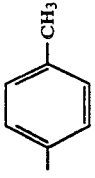
| Example No. | M | R¹ | R² | R³ | X | Y | Z | Melting point (°C.) |
|---|---|---|---|---|---|---|---|---|
| 86 | H | 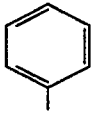 | 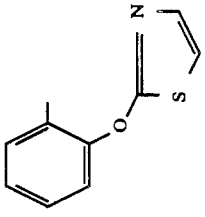 | OCH₃ | N | CH | C—OCH₃ | |
| 87 | H | 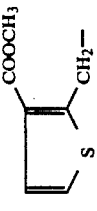 | —C₃H₇-n | OCH₃ | N | CH | C—OCH₃ | |
| 88 | H | 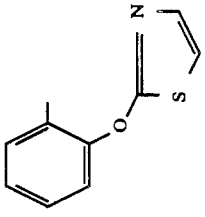 | 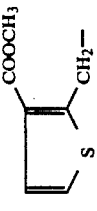 | OCH₃ | N | CH | C—OCH₃ | |
| 89 | H | 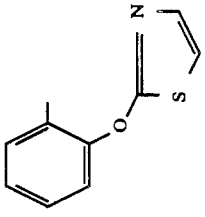 | 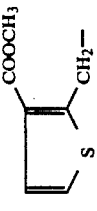 | OCH₃ | N | N | C—OCH₃ | |

TABLE 2-continued

Examples of compounds of the formula (I)

$$R^1-SO_2-N-\underset{NH}{M}-\underset{}{\overset{N-Z}{\underset{}{C}}\overset{Y}{\underset{X}{=}}\overset{}{\underset{}{C}}-R^3}$$
$$NH-SO_2-R^2$$

(I)

| Example No. | M | R$^1$ | R$^2$ | R$^3$ | X | Y | Z | Melting point (°C.) |
|---|---|---|---|---|---|---|---|---|
| 90 | H | 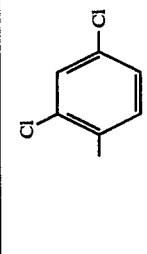 | 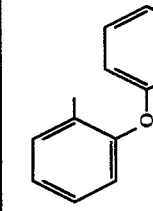 2,4-diCl-phenyl | OCH$_3$ | N | N | C—OCH$_3$ | |
| 91 | H | 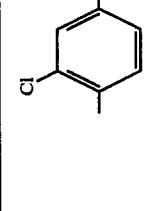 2-COOCH$_3$-phenyl | 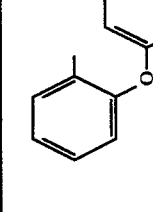 phenyl | NHCH$_3$ | N | N | C—OC$_2$H$_5$ | |
| 92 | H | 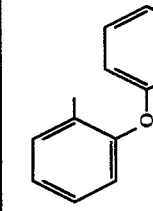 2-COOC$_2$H$_5$-phenyl | CH$_3$ | NHCH$_3$ | N | N | C—OC$_2$H$_5$ | |
| 93 | H | 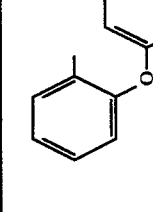 2-OSO$_2$CH$_3$-phenyl | 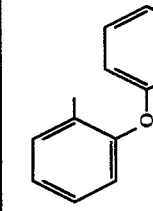 2-CN-benzyl | NHCH$_3$ | N | N | C—C$_2$H$_5$ | |

TABLE 2-continued
Examples of compounds of the formula (I)
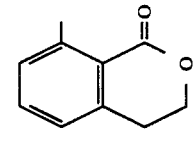
| Example No. | M | R¹ | R² | R³ | X | Y | Z | Melting point (°C.) |
|---|---|---|---|---|---|---|---|---|
| 94 | H | 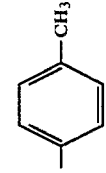 | 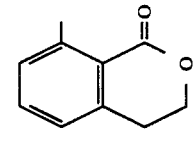 | NHCH₃ | N | N | C—OC₂H₅ | |
| 95 | H | 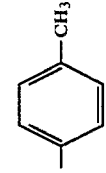-SO₂NHOCH₃ | 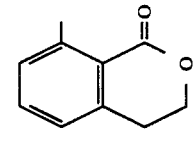 | OCH₃ | N | CH | C—OCH₃ | 164 |
| 96 | H | 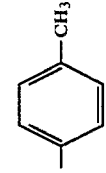-SO₂NHOCH₃ | 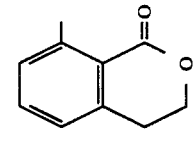 | CH₃ | N | CH | C—OCH₃ | 202 |
| 97 | H | 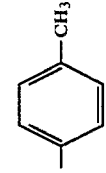-SO₂NHOC₃H₇ | 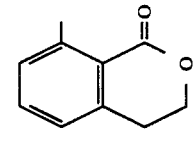 | CH₃ | N | CH | C—OCH₃ | 181 |
| 98 | H | 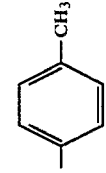-SO₂NHOCH₂CH=CH₂ |  | CH₃ | N | CH | C—OCH₃ | 148 |

TABLE 2-continued

Examples of compounds of the formula (I)

$$R^1-SO_2-N\underset{NH}{\overset{M}{\underset{\|}{N}}}\underset{C}{\overset{N-Z}{\underset{\|}{\underset{NH-SO_2-R^2}{\|}}}}\overset{Y}{\underset{X}{\|}}R^3 \quad (I)$$

| Example No. | M | R¹ | R² | R³ | X | Y | Z | Melting point (°C.) |
|---|---|---|---|---|---|---|---|---|
| 99 | H | 2-SO₂NHOCH₃-phenyl | 4-CH₃-phenyl | CH₃ | N | CH | C—OC₂H₅ | 106 |
| 100 | H | 2-SO₂NHOCH₃-phenyl | CH₃ | OCH₃ | N | CH | C—OCH₃ | |
| 101 | H | 2-SO₂NHOCH₃-phenyl | phenyl | OCH₃ | N | CH | C—OCH₃ | |
| 102 | H | 2-SO₂NHOCH₃-phenyl | phenyl | OCH₃ | N | CH | C—Cl | |
| 103 | H | 2-COOCH₃-phenyl | 4-CH₃-phenyl | CF₃ | N | CH | C—OCH₃ | 63 |

TABLE 2-continued
Examples of compounds of the formula (I)
| Example No. | M | R¹ | R² | R³ | X | Y | Z | Melting point (°C.) |
|---|---|---|---|---|---|---|---|---|
| 104 | H | 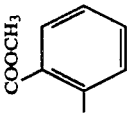 | 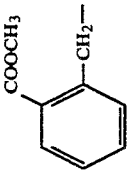 | CH₃ | N | CH | C—CH₃ | 157 |
| 105 | H | 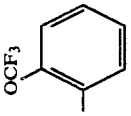 | 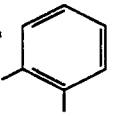 | OCH₃ | N | CH | C—OCH₃ | 211 |
| 106 | H | 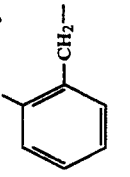 | 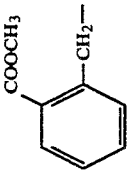 | OCH₃ | N | CH | C—OCH₃ | 147 |
| 107 | H | 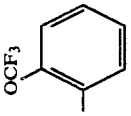 | 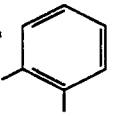 | OCH₃ | N | CH | C—OCH₃ | |
| 108 | H | 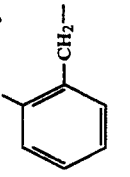 | 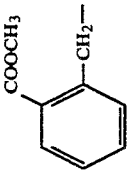 | OCH₃ | N | CH | C—OCH₃ | 160 |

TABLE 2-continued

Examples of compounds of the formula (I)

$$R^1-SO_2-N(M)-C(=N-N=Y(Z)-X-R^3)-NH-SO_2-R^2 \quad (I)$$

| Example No. | M | R¹ | R² | R³ | X | Y | Z | Melting point (°C.) |
|---|---|---|---|---|---|---|---|---|
| 109 | H | 2-Cl-C₆H₄ | 2-Cl-C₆H₄ | CH₃ | N | CH | C—OCH₃ | 168 |
| 110 | H | 2-COOCH₃-C₆H₄ | 2-COOCH(CH₃)₂-C₆H₄ | CH₃ | N | CH | C—CH₃ | 159 |
| 111 | H | 2-SO₂NHOCH₃-C₆H₄ | 2-Cl-C₆H₄ | OCH₃ | N | N | C—OCH₃ | 188 |
| 112 | H | 2-SO₂NHOCH₃-C₆H₄ | 2,4,6-(CH₃)₃-C₆H₂ | OCH₃ | N | N | C—OCH₃ | 176 |
| 113 | H | 2-SO₂NHOCH₃-C₆H₄ | C₆H₅ | OCH₃ | N | N | C—OCH₃ | 198 |

USE EXAMPLES

The compound shown below is used as the comparison substance in the following use examples:

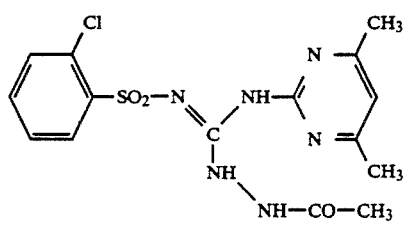

N'-(4,6-Dimethyl-pyrimidin-2-yl)-N''-acetamido-N'''-(2-chloro-phenylsulphonyl)-guanidine (known from EP-A No. 121,082).

The formulae of the compounds according to the invention used for the use examples are—with the numbering of the preparation examples ("Examples No.'-")—shown individually below.

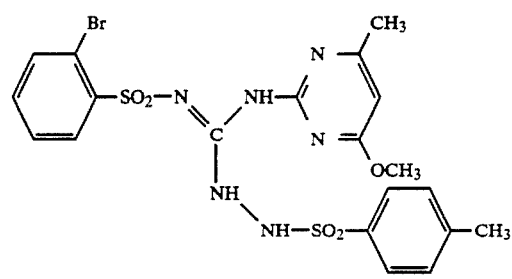

(1)

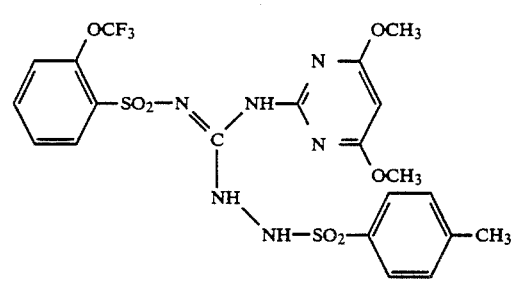

(3)

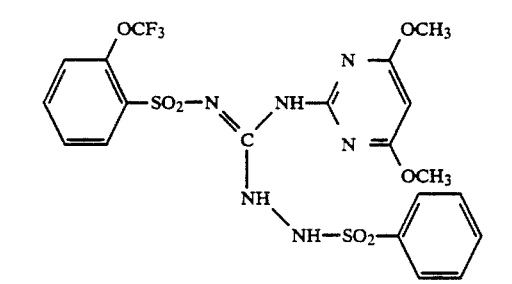

(4)

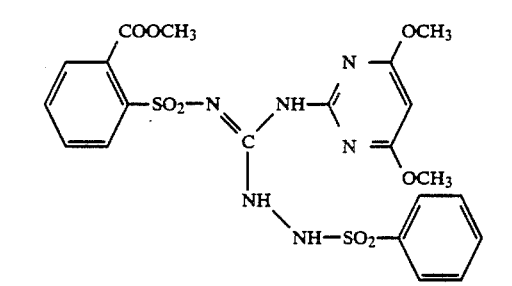

(5)

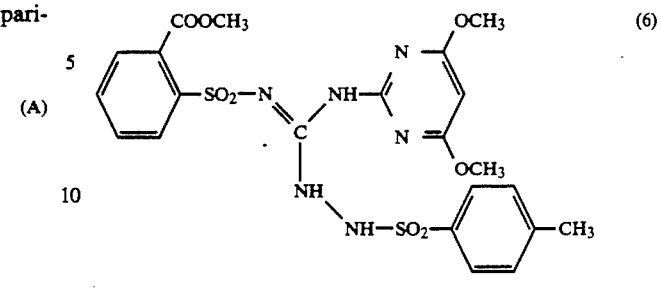

(6)

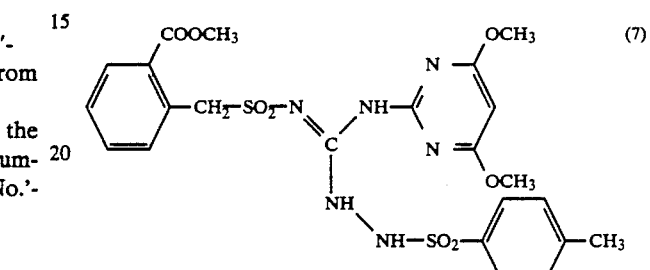

(7)

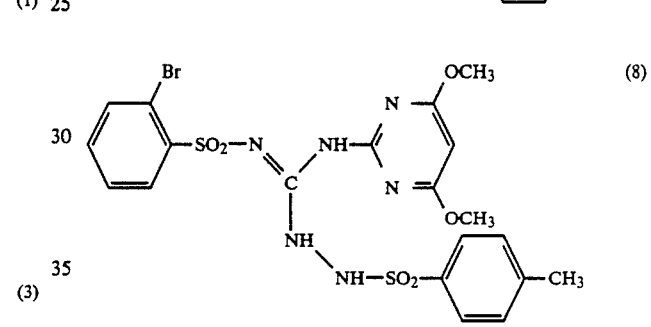

(8)

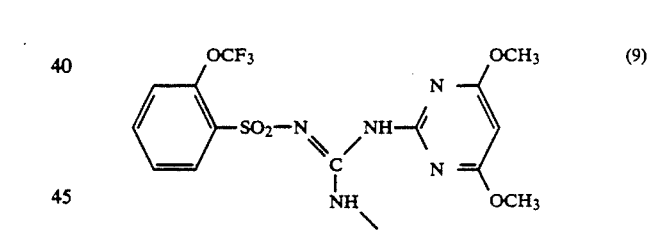

(9)

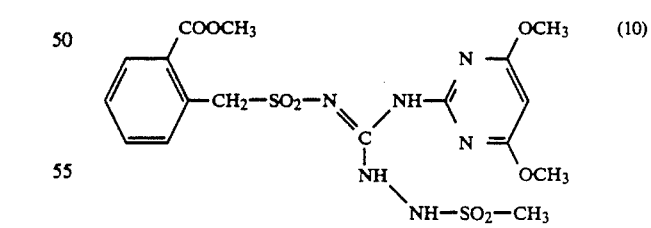

(10)

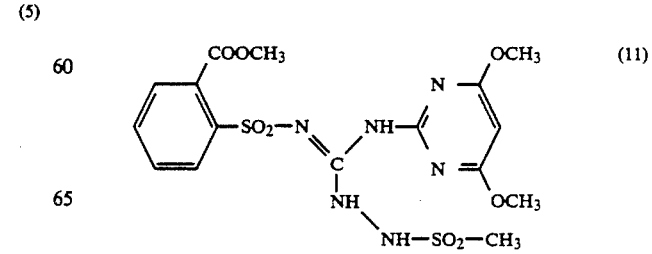

(11)

-continued

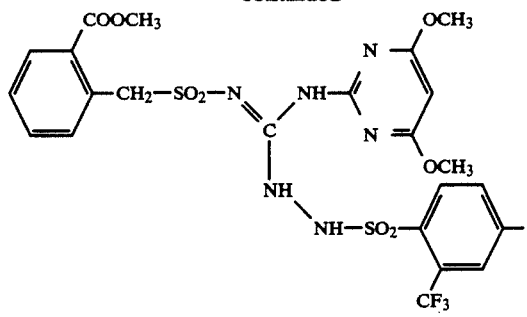 (12)

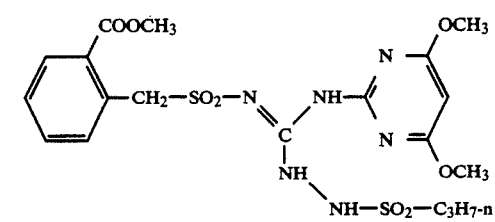 (13)

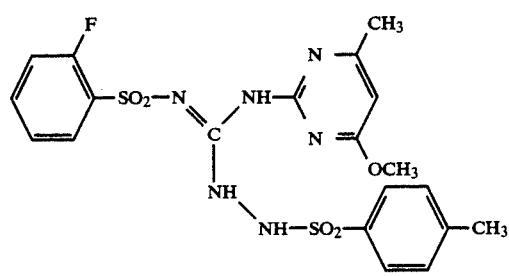 (21)

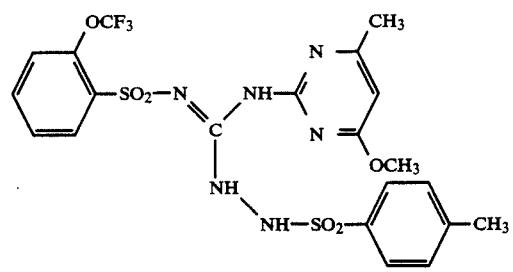 (22)

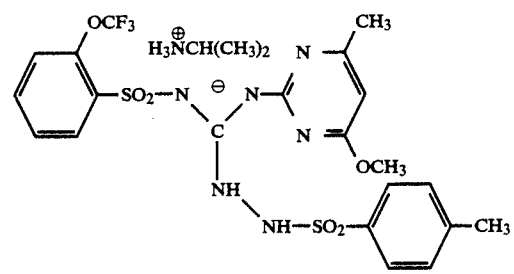 (23)

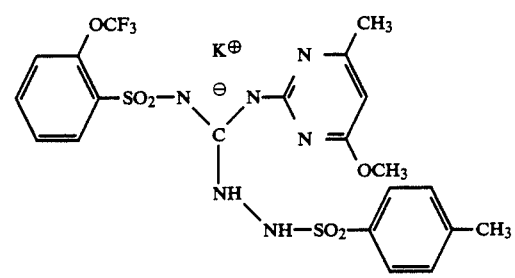 (24)

-continued

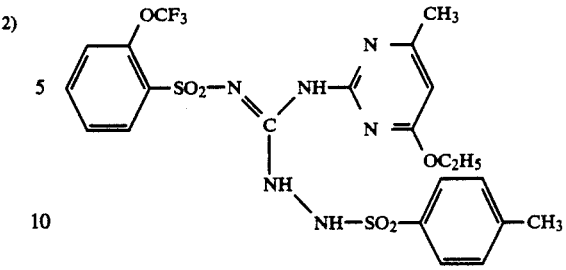 (25)

(26)

(27)

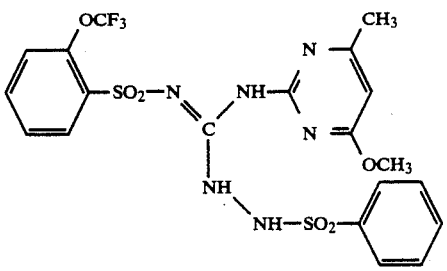 (29)

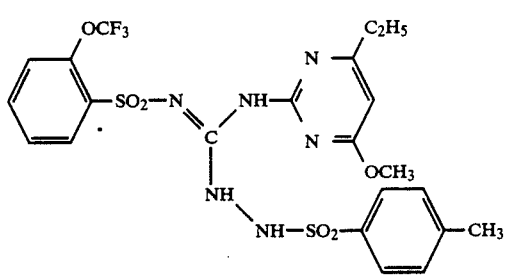 (35)

Example A

Pre-emergence test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0%=no action (like untreated control)
100%=total destruction

In this test, for example, the compounds according to the Preparation Examples (1), (3), (4), (5), (6), (7), (8), (9), (11), (21), (22), (23), (24), (25), (26), (27), (29) and (35) show considerably stronger action than the comparison substance (A).

Example B

Post-emergence test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5-15 cm are sprayed with the preparation of the active compound in such a way as to apply the particular amounts of active compound desired per unit area. The concentration of the spray liquor is so chosen that the particular amounts of active compound desired are applied in 2,000 l of water/ha. After three weeks, the degree of damage to the plants is rated in damage in comparison to the development of the untreated control. The figures denote:
0%=no action (like untreated control)
100%=total destruction In this test, for example, the compounds according to the Preparation Examples (1), (3), (4), (5), (6), (7), (8), (9), (19), (11), (12), (13), (21), (22), (23), (24), (25), (26), (27), (29) and (35) show considerably stronger action than the comparison substance (A).

Example C

Test on transplanted paddy rice

Solvent: 5 parts by weight of acetone
Emulsifier: 1 part by weight of benzyloxypolyglycol ether To produce a suitable preparation of active compound, 1 part by weight of active compound is mixed with the stated amount of solvent, the stated amount of emulsifier is added and the concentrate is diluted to the desired concentration.

Plant receptacles (surface area 1/5000 are) are filled with soil from a paddy-field. Two rice plants (variety: Kinmaze) in the 2nd-3rd leaf stage (about 10 cm tall) are transplanted into the receptacles. Seeds of *Echinochloa crush galli* and/or *Monochoria vaginalis* and/or small rhizome sections of *Eieocharis acicularis*. L are sown in the moist earth. 2 days after transplanting the rice, the soil is covered with water to a depth of 3 cm. The active compound preparation is applied to the surface of the water. The concentration of the active compound in the preparation is of no importance, only the amount of active compound applied per unit area being decisive.

After applying the active compound, a vertically descending flow of water having a velocity of 2-3 cm per day is set up through the plant receptacle for 2 days. The test batches are then kept under overflowing conditions, where the water depth is 3 cm.

After 4 weeks, the degree of damage to the plants is evaluated in % damage (or weed action) in comparison to an untreated control.

The figures denote:
0%=no action (like the untreated control)
100%=total destruction In this test, the good tolerability of the active compounds according to the invention—in particular of compounds (7) and (10)—in rice along with, at the same time, a very good weed action is apparent, whereas the very similar previously known compound (A) causes severe damage to the rice.

It will be appreciated that the instant specification and claims are set forth by way of illustration and not limitation, and that various modifications and changes may be made without departing from the spirit and scope of the present invention.

What is claimed is:

1. A sulphonylaminoguanidinoazine of the formula $$R^1-SO_2-N\underset{\underset{NH}{|}}{\overset{M}{\diagdown}}\overset{}{C}\diagdown N\diagup\underset{N=}{\overset{N=}{\diagdown}}\underset{R^3}{\overset{R^5}{\diagdown}}R^4$$

$$NH-SO_2-R^2$$

in which
$R^1$ stands for the radical $$-\underset{R^{15}}{\overset{}{C}H}-\underset{R^{16}}{\overset{R^{17}}{\diagup}}$$

wherein
$R^{15}$ stands for hydrogen,
$R^{16}$ stands for fluorine, chlorine, bromine, methyl, methoxy, ethoxy, difluoromethoxy, trifluoromethoxy, methoxycarbonyl, ethoxycarbonyl, methylsulphonyl or dimethylaminosulphonyl and
$R^{17}$ stands for hydrogen; or
$R^1$ stands for the radical $$RO-\underset{}{\overset{O}{\overset{\|}{C}}}\diagdown\underset{\underset{CH_3}{|}}{\overset{}{N}}\diagup N$$

wherein
R stands for $C_1-C_2$-alkyl;
in addition
$R^2$ stands for $C_1-C_4$-alkyl which is optionally substituted by fluorine or chlorine or for phenyl which is optionally substituted by fluorine, chlorine, bromine, $C_1$-$C_3$-alkyl, trifluoromethyl, chlorodifluoromethyl, methoxy, ethoxy, difluoromethoxy, trifluoromethoxy, amino, acetamino, methoxycarbonyl and/or ethoxycarbonyl, $R^3$ stands for hydrogen, fluorine, chlorine, bromine, methyl, trifluoromethyl, methoxy, ethoxy, difluoromethoxy, methylthio, ethylthio, ethylthioamino, methylamino, ethylamino, dimethylamino or diethylamino, $R^4$ stands for hydrogen, fluorine, chlorine or methyl, $R^5$ stands for hydrogen, fluorine, chlorine, bromine, methyl, ethyl, methoxy, ethoxy, propoxy, isopropoxy, difluoromethoxy, methylthio, ethylthio, methylamino, ethylamino, dimethylamino or diethylamino, and M stands for hydrogen or a sodium equivalent, potassium equivalent or calcium equivalent, an ammonium equivalent or a $C_1$-$C_4$-alkyl-ammonium equivalent.

2. A compound according to claim 1, wherein such compound is N′-(4,6-dimethoxy-pyrimidin-2-yl)-N″-(4-methyl-phenylsulphonylamino (-N‴-(2-methoxycarbonyl-benzylsulphonyl)-guanidine of the formula

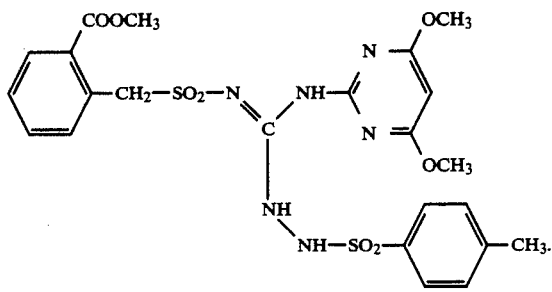

3. A herbicidal composition comprising a herbicidally effective amount of a compound according to claim 1 and a diluent.

4. A method of combating unwanted vegetation which comprises applying to such vegetation or to a habitat from which it is desired to exclude such vegetation a herbicidally effective amount of a compound according to claim 1.

5. A method of combating unwanted vegetation which comprises applying to such vegetation or to a habitat from which it is desired to exclude such vegetation a herbicidally effective amount of a compound according to claim 2.

6. A compound selected from the group consisting of N′-(4,6-dimethoxy-pyrimidin-2-yl)-N″-(dimethylaminosulphonylamino)N‴-(2-methoxycarbonylbenzylsulphonyl)-guanidine and N′-(4,6-dimethoxy-pyrimidin-2-yl)-N″-(dimethylaminosulphonylamino)N‴-(4-ethoxycarbonyl-1-methyl-pyrazol-2-yl-sulphonyl)-guanidine.

7. A compound according to claim 6 wherein such compound is N′-(4,6-dimethoxy-pyrimidin-2-yl)-N″-(dimethylaminosulphonylamino)-N‴-(2-methoxycarbonyl-benzylsulphonyl)guanidine of the formula

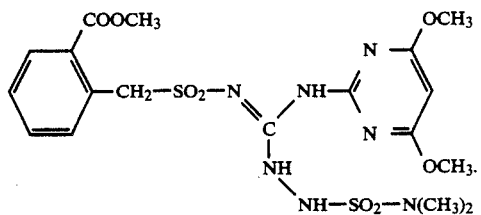

8. A compound according to claim 6, wherein such compound is N′-(4,6-dimethoxy-pyrimidin-2-yl)-N″-(dimethylaminosulphonylamino)-N‴-(4-ethoxycarbonyl-1-methyl-pyrazol-2-yl-sulphonyl)-guanidine of the formula

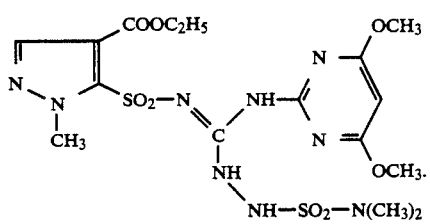

9. A herbicidal composition comprising a herbicidally effective amount of a compound according to claim 6 and a diluent.

10. A method of combating unwanted vegetation which comprises applying to such vegetation or to a habitat from which it is desired to exclude such vegetation a herbicidally effective amount of a compound according to claim 6.

* * * * *